United States Patent [19]
Tockman et al.

[11] Patent Number: 6,122,552
[45] Date of Patent: Sep. 19, 2000

[54] INSERTION APPARATUS FOR LEFT VENTRICULAR ACCESS LEAD

[75] Inventors: Bruce A. Tockman, Scandia; Randy W. Westlund, Minneapolis; Stuart R. Chastain, Shoreview, all of Minn.; Bruce M. Wilson, Escondido, Calif.; John A. Greenland, San Diego, Calif.; Jon A. Becker, Dublin, Calif.

[73] Assignee: Cardiac Pacemakers, Inc., St. Paul, Minn.

[21] Appl. No.: 09/262,155

[22] Filed: Mar. 3, 1999

[51] Int. Cl.[7] .................................................. A61B 5/042
[52] U.S. Cl. .............................................................. 607/116
[58] Field of Search .................................... 607/115, 116, 607/119, 122

[56] References Cited

U.S. PATENT DOCUMENTS

| | | |
|---|---|---|
| 5,718,862 | 2/1998 | Thompson . |
| 5,775,327 | 7/1998 | Randolph et al. . |
| 5,803,928 | 9/1998 | Tockman et al. . |
| 6,002,956 | 12/1999 | Schaer ...................................... 607/122 |

*Primary Examiner*—Scott M. Getzow
*Attorney, Agent, or Firm*—Nikolai, Mersereau & Dietz, P.A.

[57] ABSTRACT

An apparatus for positioning a cardiac lead in the vasculature of the heart includes a guide catheter, a sleeve and a guidewire. The guide catheter has an inflatable balloon at its distal end and a central lumen open distally to the exterior of the catheter for injection of dye or advancement of a guidewire through the guide catheter and past its distal end. The guide sleeve replaces the guide catheter once the guidewire is in position so that a lead can be advanced over the guidewire with the sleeve.

7 Claims, 2 Drawing Sheets

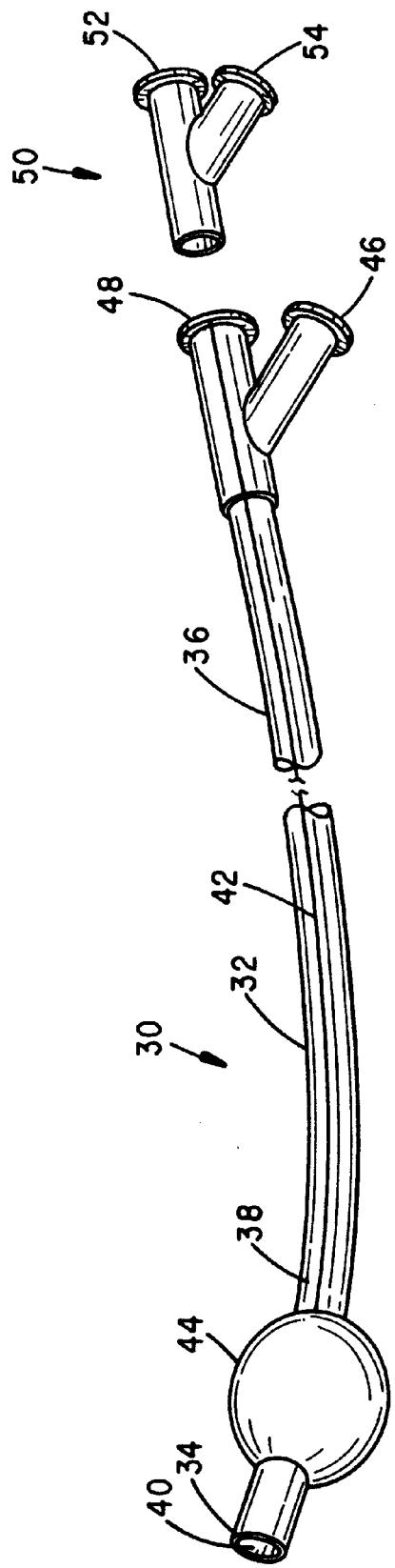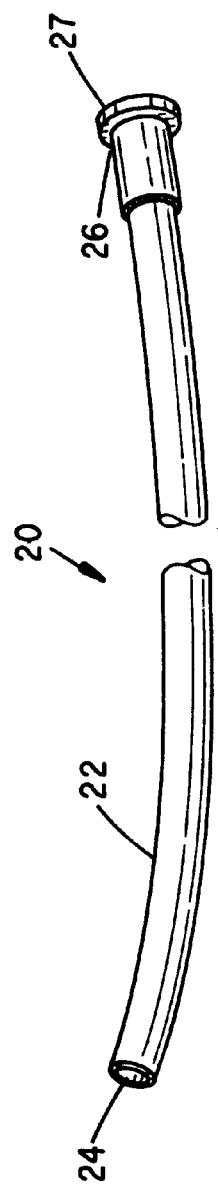
FIG. 1
FIG. 2

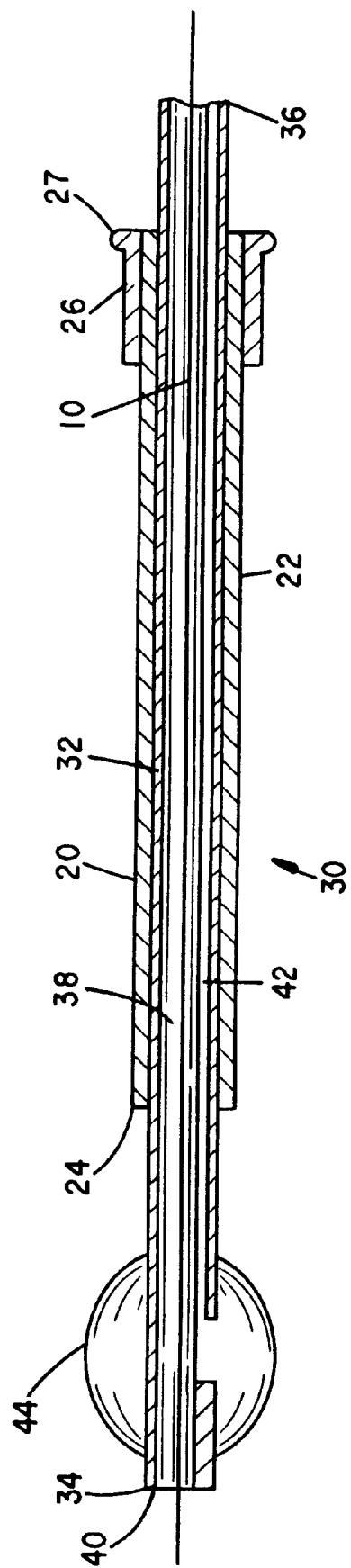
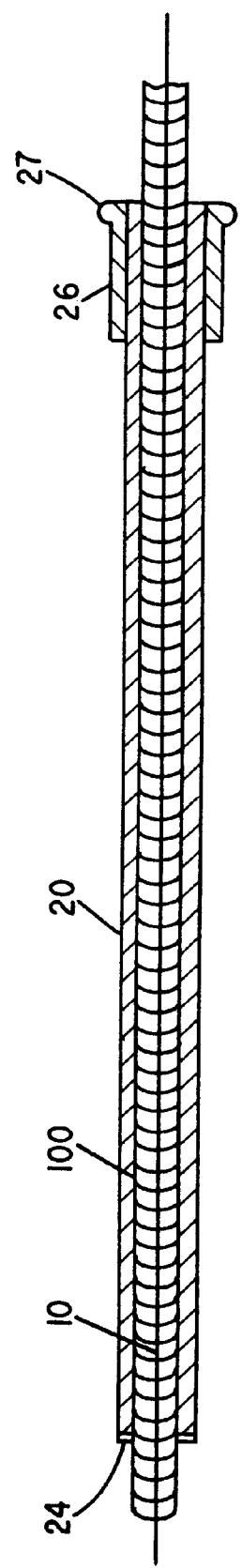
FIG. 3
FIG. 4

INSERTION APPARATUS FOR LEFT VENTRICULAR ACCESS LEAD

FIELD OF THE INVENTION

The present invention relates to leads used in conjunction with cardiac rhythm management devices. More specifically, the present invention relates to an apparatus that can be used to deploy a lead through either the superior or inferior vena cava, coronary sinus into the great vein of the heart and the veins descending therefrom toward the apex of the heart.

BACKGROUND OF THE INVENTION

In recent years various lead systems have been developed specifically designed for implantation in the vasculature of the heart. It is now known that therapeutic stimulation pulses can be delivered to the left side of the heart using a lead advanced through the coronary sinus and great vein of the heart. Such leads can be used as part of a pacing protocol for the treatment of congestive heart failure or to defibrillate the left ventricle.

The path through the vena cava, coronary sinus and great vein is somewhat narrow and includes many turns. As a result, there exists a need for an apparatus which assists the surgeon in advancing the lead along this path.

In the past, various guidewires have been used to position cardiac leads. Also, guide catheters have also been used. See, for example, U.S. Pat. No. 5,775,327 to Randolph et al. However, the apparatus used in the prior art imposed serious size restrictions on the lead, particularly when the lead was to be positioned at or beyond the coronary sinus. The present invention provides an apparatus which simplifies insertion of the lead and allows a larger diameter lead to be used.

SUMMARY OF THE INVENTION

The present invention relates to an apparatus specifically designed to assist the surgeon when implanting a cardiac lead within the vasculature of the heart. The apparatus includes a guidewire, a specially designed guide catheter and a unique sheath. When the apparatus is used, the first step is to advance the guide catheter through the vasculature until its distal tip enters the coronary sinus. A balloon associated with the distal tip is then inflated to (a) hold the catheter in place and (b) block the flow through the coronary sinus past the balloon. Next, to create a map of the venous anatomy through which the lead will ultimately be advanced, dye is injected through the central lumen of the catheter. Third, the balloon is deflated to permit a guidewire to be advanced through the lumen of the catheter past the coronary sinus and into one of the coronary veins of the heart. Once the guidewire is in place, a long sheath is slid forward over the shaft of the guide catheter until the distal tip of the sheath seats in the coronary sinus. The guide catheter is then removed leaving the guidewire and sheath in place. Finally, the lead is advanced over the guidewire and through the sheath. A larger diameter lead can be inserted because of the relatively large diameter of the sheath. Once the lead reaches its final position, the guidewire and sheath are removed.

A better understanding of the apparatus of the present invention will be gained from a review of the following detailed description of the invention in light of the accompanying drawings. This detailed description is not intended to be limiting, but rather is provided to comply with the disclosure requirements of the patent statutes.

BRIEF DESCRIPTION OF THE DRAWINGS

FIG. 1 is a side view of the guide catheter of the present invention.

FIG. 2 is a side view of the sleeve of the present invention.

FIG. 3 is a cross-sectional view showing the guide catheter, guidewire and sleeve in assembled relation.

FIG. 4 is a cross-sectional view showing the guidewire and sleeve in combination with a cardiac lead.

DETAILED DESCRIPTION OF THE PREFERRED EMBODIMENTS

The apparatus of the present invention includes three main components, a guidewire 10, a sleeve 20 and a guide catheter 30. The guidewire 10 is of a standard design. The sleeve 20 and guide catheter 30 are uniquely designed to cooperate with the guidewire 10 to assist in placement of a left ventricular access lead 100.

The design of the guide catheter 30 is generally shown in FIGS. 1 and 3. As can be seen from these drawings, the guide catheter 30 includes an elongated tube 32 having a distal end 34 and a proximal end 36. The tube 32 has a central lumen 38. The distal end 34 of the tube has an orifice 40 which is in communication with the central lumen 38. The tube 32 also has a side lumen 42 in communication with an inflatable balloon 44 associated with the distal end 34 of the tube 32.

The proximal end 36 of tube 32 includes two ports 46 and 48. Port 48 is in communication with the central lumen 38. Port 46 is in communication with the side lumen 42. Port 46 is used for inflation and deflation of the balloon 44 via the side lumen 42. Port 48 is used in a number of ways. For example, it can be used to inject dye. It also provides a path for insertion of the guidewire 10. The port 48 can also be coupled to a hemostatis adapter 50 which includes ports 52 and 54. Port 52 is specifically designed for insertion of the guidewire 10. Port 54 is specifically designed for dye injection. The use of the adapter 50 permits the surgeon to inject dye even when the guidewire 10 is positioned in the central lumen 38 of the guide catheter 30.

The guide catheter 30 of the present invention is constructed to have the necessary size, shape and flexibility to permit the distal end 34 of the guide catheter 30 to be inserted into the coronary sinus from either an inferior or superior vena cava approach. Once the distal end 34 is inserted into the coronary sinus, the balloon 44 is inflated to temporarily block the back flow of blood through the coronary sinus. Next dye is injected through the central lumen 38. As the dye exits the orifice 40 at the distal end of the central lumen, it "illuminates" the coronary veins so that the surgeon can determine the appropriate path to be followed when inserting the guidewire 10. The balloon 44 is then deflated and the guidewire 10 is inserted through the central lumen 38. When the adapter 50 is used, the surgeon can periodically reinflate the balloon 44 and inject more dye to check the placement of the guidewire 10 or again view the path to be followed as the guidewire 10 is advanced.

The sleeve which resides over the shaft of the guide catheter 20 is a thin walled peel-away or non-peel-away tube 22 having a distal end 24 which is open and a proximal end 26. The sleeve 20 is flexible near the distal end 24 and stiffer near the proximal end 26. The flexible distal end 24 allows the sleeve to conform to the shape of the distal end 34 of the guide catheter 30 and makes it non-traumatic to the coronary sinus. The proximal termination can be a peel-away luer fitting 27 or a fixed luer fitting.

Once the guidewire 10 is in place, the desired position in the vein, the sleeve 20 is advanced forward over the guide catheter 30 into the opening of the coronary sinus. The guide catheter 30 is removed once the sleeve 20 is properly positioned leaving both the sleeve 20 and guidewire 10 in place. The guidewire 10 will, of course, be located within the sleeve 20 and extend both proximally and distally from the sleeve 20. Next, the pacing lead 100 is inserted over the guidewire 10 and inside the sleeve 20 until the electrodes on the lead 100 reach the proper position in the vein. The sleeve 20 and guidewire 10 are then retracted leaving the lead 100 in place. In the alternative embodiment, the sleeve can be peeled away to leave the lead in place. If a non-over-the-wire lead is used, the guidewire will be removed prior to inserting the lead into the sleeve.

Various materials can be used in the construction of the sleeve 20 and guide catheter 30. The sleeve 20, for example, could be made of polytetrafluoroethylene, a material known for its lubricious nature. Use of such a material will reduce the amount of frictional resistance encountered when inserting the sleeve 20, retracting the guide catheter 30, implanting the lead 100, and retracting the sleeve 20. The guide catheter 30 can be constructed in a number of ways. For example, it can include a braided material sandwiched between internal and external polymer tubes. Suitable polymers include, but are not limited to, polytetrafluoroethylene and polyurethane. The braiding is provided so that torque can be transmitted through the catheter during insertion. The braiding will preferably stop short of the distal end so that the distal end is atraumatic.

The foregoing discussion is intended to illustrate the preferred embodiment of the invention. Various modifications can be made without departing from the invention. Thus, the invention is limited only by the scope of the following claims which are intended to cover all alternative embodiments and modifications as may fall within the true scope of this invention.

What is claimed:

1. An apparatus for insertion of a left ventricular access lead through the coronary sinus into the vasculature of the left side of the heart comprising:

(a) a guidewire;

(b) a guide catheter including (i) an elongated tube having a proximal end, a distal end, a first lumen, and a second lumen and an orifice through the distal end of said tube and in communication with said first lumen; (ii) an inflatable balloon coupled to said tube and in communication with said second lumen; and (iii) first and second ports at the proximal end of said tube, said first ports in communication with said first lumen and said second port in communication with said second lumen, said first port, first lumen and orifice sized to that said guidewire can be inserted through said first port and first lumen and pass through the orifice post the distal end of said guide catheter, said second port adapted so that it can be used to inflate and deflate said balloon via said second lumen, said tube being of a sufficient length so that inflation of the balloon can serve to temporarily close off the coronary sinus to prevent backflow through the coronary sinus; and (c) a thin walled sleeve comprising a tube having a proximal end and a distal end and sized to be advanced over the guide catheter until its distal end reaches the coronary sinus, said thin walled sleeve configured to be left in place during retraction of the guide catheter and removed once said lead is inserted in its proper position through said sleeve.

2. The apparatus of claim 1 wherein said orifice, first lumen, and first port can be used to inject dye into the area past the coronary sinus when the balloon is inflated to block backflow through the coronary sinus.

3. The apparatus of claim 1 further including an adapter that can be coupled to the first port so that dye can be injected via the first lumen and orifice past the guide catheter when the guidewire is present in the first lumen.

4. The apparatus of claim 1 wherein said sleeve is a thin walled peel-away tube.

5. The apparatus of claim 1 wherein said sleeve is flexible near its distal end and stiffer near its proximal end so that the sleeve can be advanced over the guide catheter and the distal end is non-traumatic to the coronary sinus.

6. The apparatus of claim 1 wherein said guide catheter is used in positioning the guidewire and sleeve so that the guidewire and sleeve are used to position a lead.

7. A method for insertion of a left ventricular access lead having at least one lumen through the coronary sinus into the vasculature of the left side of the heart comprising:

(a) advancing the distal end of a guide catheter through the vasculature of the heart until the distal end of the guide catheter enters the coronary sinus of the heart, said guide catheter having a balloon associated with the distal end and at least one lumen;

(b) inflating the balloon of the guide catheter to hold the catheter in place and inhibit flow through the coronary sinus past the balloon;

(c) injecting dye through a lumen of the catheter past the distal end of the catheter to create a map of the venous anatomy through which said lead will ultimately be abandoned;

(d) advancing a guidewire through a lumen of the catheter past the distal end of the catheter and into one of the coronary veins of the heart;

(e) sliding the distal end of a sheath forward over the guide catheter until the distal end of the sheath seats in the coronary sinus;

(f) removing the guide catheter while the guidewire and sheath are left in place;

(g) inserting the guidewire through the distal end of the lead into a lumen of said lead and advancing a lead over the guidewire and through the sheath until the distal end of the lead reaches the desired position; and (h) removing the guidewire and sheath while leaving the lead in place.

* * * * *

UNITED STATES PATENT AND TRADEMARK OFFICE
CERTIFICATE OF CORRECTION

PATENT NO. : 6,122,552  
DATED : September 19, 2000  
INVENTOR(S) : Bruce A. Tockman, et al.

Page 1 of 1

It is certified that error appears in the above-identified patent and that said Letters Patent is hereby corrected as shown below:

In the printed patent under "Inventors" the name of "John A. Greenland" should read --John S. Greenland--

<u>Claim 1, Column 3,</u>  
Line 53 delete "to" and insert --so--.

Signed and Sealed this

Third Day of July, 2001

*Attest:*

*Attesting Officer*

NICHOLAS P. GODICI  
*Acting Director of the United States Patent and Trademark Office*